US012699054B2

(12) United States Patent
Royer

(10) Patent No.: US 12,699,054 B2
(45) Date of Patent: Aug. 4, 2026

(54) STABILIZED N,N-DIETHYL-P-PHENYLENEDIAMINE SOLUTION AND METHOD FOR DETECTING CHLORINE

(71) Applicant: HACH COMPANY, Loveland, CO (US)

(72) Inventor: Douglas Royer, Gilbert, IA (US)

(73) Assignee: HACH COMPANY, Loveland, CO (US)

( * ) Notice: Subject to any disclaimer, the term of this patent is extended or adjusted under 35 U.S.C. 154(b) by 738 days.

(21) Appl. No.: 18/090,163

(22) Filed: Dec. 28, 2022

(65) Prior Publication Data

US 2024/0219309 A1 Jul. 4, 2024

(51) Int. Cl.
*G01N 21/78* (2006.01)
*G01N 33/18* (2006.01)

(52) U.S. Cl.
CPC ............. *G01N 21/78* (2013.01); *G01N 33/18* (2013.01)

(58) Field of Classification Search
CPC ....... G01N 21/78; G01N 33/18; G01N 33/182
See application file for complete search history.

(56) References Cited

U.S. PATENT DOCUMENTS 3,615,572 A 10/1971 Bimmler et al.
4,248,681 A * 2/1981 Sweeney .................. C25B 1/26 204/260
6,130,029 A 10/2000 LeBlanc, Jr.
8,987,000 B2 3/2015 Evtodienko et al.
8,993,337 B2 3/2015 Evtodienko et al.
2014/0083864 A1 3/2014 Rowhani et al.
2015/0344333 A1* 12/2015 Xia ...................... C25B 11/075 210/192

FOREIGN PATENT DOCUMENTS

| | | | |
|---|---|---|---|
| CN | 102128833 | A | 7/2011 |
| CN | 106323954 | A | 1/2017 |
| CN | 113984755 | B | 4/2022 |
| DE | 2502467 | A1 | 7/1976 |
| EP | 3 036 541 | A1 | 6/2016 |
| JP | 2004-85453 | A | 3/2004 |
| JP | 4588776 | B2 | 12/2010 |
| JP | 2011-043482 | A | 3/2011 |

(Continued)

OTHER PUBLICATIONS

Best et al. "Stabilisation of DPD (N,N-Diethyl-p-phenylenediamine Sulphate) Reagent For the Determination of Free Available Residual Chlorine in Water". Analyst, vol. 110, Feb. 1985, pp. 221-222.

(Continued)

*Primary Examiner* — Samuel P Siefke
(74) *Attorney, Agent, or Firm* — Oliff PLC

(57) ABSTRACT

A reagent for chlorine analysis includes N,N-diethyl-p-phenylenediamine (DPD), an inorganic chloride salt at a concentration of 0.5 M or more, and water. Additionally, a method for detecting chlorine in an aqueous sample includes subjecting a test sample to photometry. The test sample includes the aqueous sample; and a DPD reagent that includes DPD, an inorganic chloride salt at a concentration of 0.5 M or more, and water. The reagent and detection method can be used with minimal or no strong acids.

16 Claims, 1 Drawing Sheet

(56) References Cited

FOREIGN PATENT DOCUMENTS

| | | | |
|---|---|---|---|
| JP | 5496574 | B2 | 5/2014 |
| WO | 00/52464 | A1 | 9/2000 |
| WO | 2012/053028 | A1 | 4/2012 |
| WO | 2015/023362 | A1 | 2/2015 |

OTHER PUBLICATIONS

Material Safety Data Sheet for DPD #4 Tablet, Lamotte, Sep. 15, 2009, pp. 1-5.

Hill et al. "Rapid Test Paper Methods for Hydrogen Cyanide in the Atmosphere". The Annals of Occupational Hygiene, vol. 14., Issue 4, Dec. 1971, pp. 289-294 (abstract only).

* cited by examiner

STABILIZED N,N-DIETHYL-P-PHENYLENEDIAMINE SOLUTION AND METHOD FOR DETECTING CHLORINE

BACKGROUND

In certain applications, it may be important to monitor the presence of chlorine as a contaminant or to ensure that chlorine is at a desired concentration. For example, chlorine detection is frequently used to monitor pool water, drinking water, and water used for hemodialysis.

The DPD (N,N-diethyl-p-phenylenediamine) method for testing chlorine levels was introduced in 1957, and has become the most widely used method for determining free and total chlorine in water. DPD test methods are based on liquid test kits that involve mixing a sample of water with chemicals dispensed from a dropper bottle and reading the color developed with a photometer. Specifically, the water sample is mixed with a mixture of a DPD reagent (containing the DPD) and a buffer reagent.

The DPD reagent is prepared by mixing dry DPD with an indicator solution, which usually includes a strong acid used to stabilize the DPD. The DPD reagent will turn pink when contacted with a sample containing chlorine, indicating the presence of chlorine. The amount of chlorine present in the sample can be estimated by photometry using a chlorine analyzer, where a darker pink color indicates that more chlorine is present in the sample. The chlorine analyzer measures the free residual chlorine ($OCl^-$ and HOCl) and the total residual chlorine (free chlorine+combined chloramines) in the sample.

However, the DPD reagent is highly unstable and will discolor over time once prepared. This discoloration can lead to inaccurate results because it is difficult to interpret whether the discoloration is due to the presence of chlorine or the result of the reagent destabilizing. For this reason, the DPD reagent is not prepared until immediately before measurements need to be taken.

The buffer reagent is included to balance the pH of the mixture. Generally speaking, the pH of the test sample (containing the DPD reagent and water sample) should be in the range of 6-7 to ensure accurate measurements with the chlorine analyzer. Thus, the buffer reagent is included to adjust the pH of the test sample to fall within this range.

As discussed above, the DPD reagent is highly unstable and is therefore not prepared until immediately before measurements need to be taken. This means that the end user must prepare the DPD reagent from the dry DPD and indicator solution, exposing the end user to both strong acids and the DPD powder. These materials are hazardous to handle.

What is needed is a more stable liquid formulation of DPD that can be safely handled by the end user. The DPD formulation can be prepared in advance and stored, sold, and shipped to the end user, eliminating the need for the end user to prepare the DPD reagent.

SUMMARY

The disclosed embodiments describe a reagent for chlorine analysis, and a method for detecting chlorine in an aqueous sample.

According to one aspect of the embodiments, a reagent for chlorine analysis includes N,N-diethyl-p-phenylenediamine (DPD), an inorganic chloride salt at a concentration of 0.5 M or more, and water.

Another aspect of the embodiments includes a method for detecting chlorine in an aqueous sample includes subjecting a test sample to photometry. The test sample includes the aqueous sample; and a DPD reagent that includes DPD, an inorganic chloride salt at a concentration of 0.5 M or more, and water.

BRIEF DESCRIPTION OF THE DRAWINGS

A more particular description of the invention will be rendered by reference to specific embodiments thereof that are illustrated in the appended drawings. Understanding that these drawings depict only typical embodiments of the invention and are not therefore to be considered to be limiting of its scope, embodiments of the invention will be described and explained with additional specificity and detail through the use of the accompanying drawings in which.

DETAILED DESCRIPTION OF EMBODIMENTS

Figure 2:
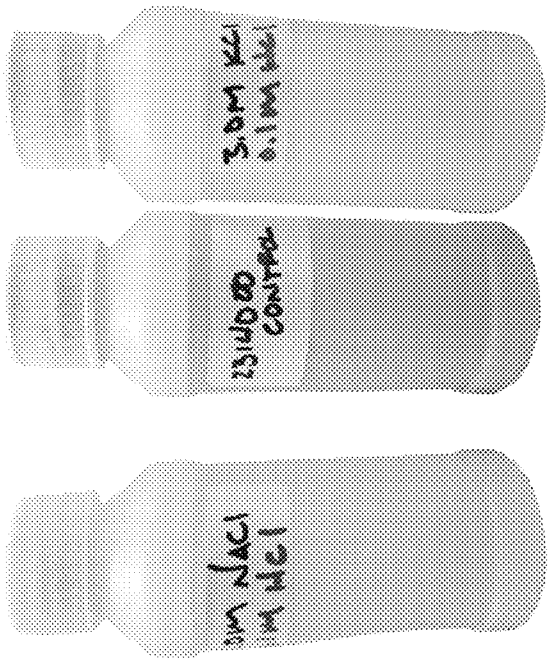
FIG. 2 is a photograph showing the results of an experiment in which the ability of NaCl and KCl to stabilize DPD was studied in indicator solutions at elevated temperatures and for extended periods of time.

The conventional DPD reagent used for chlorine analysis is highly unstable and will discolor over time once prepared, leading to inaccurate results. Accordingly, the DPD reagent is not prepared until immediately before measurements need to be taken. As a result, the end user must prepare the DPD reagent from the dry DPD and indicator solution, exposing the end user to hazardous materials. The inventor conducted several studies to determine the cause of the DPD reagent discoloration and to develop a formulation that does not suffer from this same problem.

Without being bound by theory, it is the inventor's belief that the DPD reagent becomes unstable and discolors due to dimerization of the DPD. The structure of DPD is shown below.

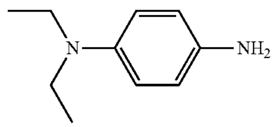

It is believed that the amine groups in two DPD molecules will dimerize if the DPD molecules are not otherwise stabilized.

Conventionally, a strong acid is included in the indicator solution in order to stabilize the solubilized DPD. As used herein, a "strong acid" is an acid that is completely dissociated or ionized in an aqueous solution. It is a chemical species with a high capacity to lose a proton, $H^+$. Examples include HCl (hydrochloric acid), $H_2SO_4$ (sulfuric acid), $HNO_3$ (nitric acid), HBr (hydrobromic acid), $HClO_4$ (perchloric acid), HI (hydroiodic acid), p-toluenesulfonic acid (pTSA), and methanesulfonic acid.

It is believed that the strong acid protonizes the DPD amine groups, preventing dimerization. However, the strong acid lowers the pH of the DPD reagent, leading to the need for a buffer agent in order to adjust the pH of the mixture to be within the desired measurement range of 6-7. The strong acid is also hazardous to handle.

Through various studies, the inventor found that, surprisingly, DPD can be stabilized in the indicator solution for extended periods of time by the inclusion of an inorganic salt. Specific embodiments are described below to facilitate understanding, but the present invention is not limited to those embodiments.

Indicator Solution

The indicator solution can be prepared in advance of preparing the DPD reagent, or the indicator solution can be prepared as part of the process of preparing the DPD reagent. The indicator solution functions as a diluent and carrier for the DPD.

The indicator solution includes water. For example, the indicator solution is an aqueous solution comprising at least 50 wt % water, such as 60 wt %, 70 wt %, 80 wt %, 90 wt %, 95 wt % or more. The indicator solution can include 50 to 98 wt %, 60 to 95 wt %, or 70 to 90 wt % water, for example.

The indicator solution further includes an inorganic salt, and particularly an inorganic salt formed from the reaction of a strong acid with a strong base. Here, a "strong base" is a fully ionic base that is completely dissociated in an aqueous solution. The inorganic salt is preferably a chloride salt, and is more preferably sodium chloride (NaCl) or potassium chloride (KCl).

It was found that chloride salts in particular provide surprising improvements in the stability of the DPD solution. It is believed that the salt interacts with the amine groups in the indicator solution, preventing dimerization of the DPD. This reduces the need for a strong acid, which in turn reduces the need for a buffer reagent.

The indicator solution may optionally include one or more strong acids. The strong acid(s) may be present in the indicator solution at a total concentration of 0.5 M, 0.4 M, 0.3 M, 0.2 M, 0.1 M or less. For example, the strong acid(s) may be present at a total concentration of 0.05 to 0.50 M, 0.10 to 0.45 M, or 0.20 to 0.40 M. The type of strong acid is not limited and may be any one of the strong acids mentioned above.

The indicator solution includes the inorganic salt (e.g., NaCl or KCl) at a concentration up to 10.0 M. For example, the inorganic salt concentration may be 0.5 M, 1.0 M, 2.0 M, 3.0 M, 4.0 M, 5.0 M or more. The inorganic salt can be included in amounts ranging from 0.5 to 7.5 M, 0.1 to 5.0 M, or 2.0 to 4.5 M, for example.

The amount of inorganic salt in the indicator solution may be adjusted based on the concentration of the strong acid. For example, the molar ratio of inorganic salt to strong acid in the indicator solution may be approximately 100:1, 50:1, 40:1, 30:1, 20:1, or 10:1.

DPD Reagent

The DPD reagent includes the indicator solution and the dry DPD mixed therein. As mentioned above, the indicator solution can be prepared in advance of preparing the DPD reagent, or the indicator solution can be prepared as part of the process of preparing the DPD reagent. For example, the indicator solution solutes (e.g., inorganic salt and strong acid) and DPD can be added to the aqueous solution sequentially or in combination. The amounts of water, inorganic salt, and strong acid in the DPD reagent are approximately the same as the respective amounts in the indicator solution.

The DPD reagent includes the DPD at a concentration of about 20 g/L, 30 g/L, 40 g/L, 50 g/L, 75 g/L, 100 g/L or more. The molar ratio of DPD to inorganic salt in the DPD reagent can range from 1:5 to 1:40, 1:10 to 1:30, or 1:15 to 1:25, for example. The molar ratio of DPD to strong acid (if included) in the DPD reagent can range from 2:1 to 1:5, 1.5:1 to 1:3, or 1:1 to 1:2, for example.

The DPD reagent remains stable under typical storage conditions for at least 30 days, and preferably 3 months, 6 months, 12 months, 24 months or longer. Typical storage conditions can include temperatures ranging from 0° C. to 40° C., such as room temperature (20° C.). "Stable" as used here means that there is no color development in the DPD indicator solution that will cause a false positive interference when reading the color development of the DPD-chlorine reaction. "Stable" also means that the DPD indicator solution has not degraded over time to give a false negative reading due to low recovery on a chlorine-containing sample.

Buffer Reagent

The DPD reagent can be mixed with a buffer reagent prior to photometric analysis. For example, if the pH of the DPD reagent is less than 6, a buffer reagent can be added to the DPD reagent until the pH of the mixture is in the range of 6-7.

The buffer reagent includes a buffering agent in water. The buffering agent can be a salt of a weak acid and a weak base. Examples are potassium salts, carbonates, bicarbonates, and hydrogen phosphates. Weak acids such as carboxylic acid (e.g., maleic acid, citric acid, formic acid, fumaric acid) and sulfamic acid can also be used as buffering agents. The buffering agent can be, for example, sulfamic acid/sulfamate, formic acid/formate, acetic acid/acetate, dihydrogen phosphate/hydrogen phosphate, ammonium/ammonia, bicarbonate/carbonate, fumaric acid/hydrogen fumarate, benzoic acid/benzoate, or 2-(N-morpholino)ethanesulfonic acid (MES).

Method for Detecting Chlorine in an Aqueous Sample

The DPD reagent (and optionally a buffer reagent) can be added to an aqueous sample for the purpose of detecting any chlorine present in the aqueous sample. The aqueous sample might contain chlorine in an amount ranging from, for example, 0.0 to 10.0 mg/L, 0.1 to 5.0 mg/L, 0.2 to 4.0 mg/L, 0.3 to 2.0 mg/L, or 0.5 to 0.7 mg/L. The DPD reagent, optional buffer reagent, and aqueous sample together form the test sample, which is subjected to photometric analysis using a chlorine analyzer.

Analysis is typically performed around room temperature using a test sample with a pH adjusted to 6-7.

EXAMPLES

The inventor conducted the following experiments, which demonstrate that the DPD reagent can be stabilized by the inclusion of NaCl.

Example 1

The stabilizing effect of NaCl was measured using different concentrations of NaCl in indicator solutions. The indicator solutions included 0.1 M, 0.2 M, 1.0 M, or 2.0 M NaCl in deionized water. The indicator solutions did not include any acid. DPD was added to the indicator solutions at a concentration of 0.1M. After storing the solutions at 25° C. for 2 weeks, the solutions were visually observed for the presence of any pink hue. The results are shown in FIG. 1.

Figure 1:
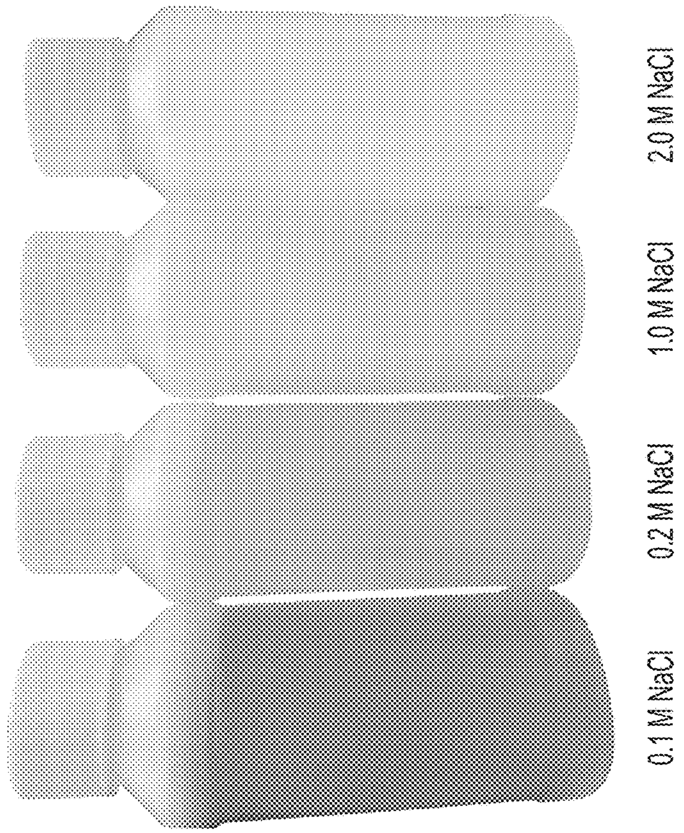
FIG. 1 is a photograph showing the results of an experiment in which the ability of NaCl to stabilize DPD was measured using different concentrations of NaCl in indicator solutions.

As can be seen in FIG. 1, the NaCl stabilized the DPD in solution. The higher the concentration of the NaCl, the less pink was observed. When NaCl was included at a concentration of 2.0 M, no pink coloration was observable by the naked eye after 2 weeks at 25° C. Thus, it was found that NaCl could be used to stabilize DPD without using any acid. And if NaCl is included at higher concentrations, the solution will remain stable for even longer periods of time. As a result, a ready-made indicator solution can be provided to the end user, eliminating the need for handling hazardous acids or DPD powder.

Example 2

The stabilizing effect of NaCl and KCl was studied in indicator solutions at higher temperatures and for longer periods of time. The test solutions included 3.0 M inorganic salt (either NaCl or KCl) and 0.1 M HCl in deionized water. The control solution included 0.53 M pTSA in deionized water. HCl and pTSA provide comparable effects in stabilizing DPD. DPD was added to the indicator solutions at a concentration of 0.1 M. After storing the solutions at 40° C. for 4 weeks, the solutions were visually observed for the presence of any pink hue. The results are shown in FIG. 2.

As can be seen in FIG. 2, the test solutions containing inorganic salt more effectively stabilized the DPD as compared to a conventionally stabilized solution including only a strong acid (pTSA). When NaCl or KCl was included at a concentration of 3.0 M, no pink coloration was observable by the naked eye after 4 weeks at 40° C. Thus, it was found that chloride salts such as NaCl and KCl could be used to stabilize DPD over extended periods of time and even at elevated temperatures, particularly if combined with small amounts of a strong acid. And if the salt is included at higher concentrations or the solution is stored at lower temperatures (e.g., room temperature), the solution will remain stable for even longer periods of time. As a result, a ready-made indicator solution can be provided to the end user, eliminating the need for handling hazardous acids or DPD powder.

While the invention has been described in conjunction with the specific exemplary embodiments thereof, it is evident that many alternatives, modifications, and variations will be apparent to those skilled in the art. Accordingly, exemplary embodiments of the invention as set forth herein are intended to be illustrative, not limiting. There are changes that may be made without departing from the spirit and scope of the invention.

What is claimed is:

1. A reagent for chlorine analysis, the reagent comprising:
N,N-diethyl-p-phenylenediamine (DPD);
an inorganic chloride salt at a concentration of 1.0 M or more; and
water.

2. The reagent of claim 1, wherein the reagent is stable for at least 30 days at 20° C.

3. The reagent of claim 1, further comprising one or more strong acids at a total concentration of 0.3 M or less.

4. The reagent of claim 3, wherein the total concentration of the one or more strong acids in the reagent is 0.2 M or less.

5. The reagent of claim 3, wherein the total concentration of the one or more strong acids in the reagent is 0.1 M or less.

6. The reagent of claim 1, not comprising any strong acids.

7. The reagent of claim 1, wherein the inorganic chloride salt is NaCl or KCl.

8. The reagent of claim 1, wherein the inorganic chloride salt is NaCl.

9. The reagent of claim 1, wherein the inorganic chloride salt is KCl.

10. The reagent of claim 1, wherein the concentration of the inorganic chloride salt in the reagent is 2.0 M or more.

11. The reagent of claim 1, wherein the concentration of the inorganic chloride salt in the reagent is 3.0 M or more.

12. The reagent of claim 3, wherein a molar ratio of the inorganic chloride salt to the one or more strong acids in the reagent is 30:1 or more.

13. The reagent of claim 3, wherein a molar ratio of the inorganic chloride salt to the one or more strong acids in the reagent is 50:1 or more.

14. The reagent of claim 1, wherein a concentration of the DPD in the reagent is 20 g/L or more.

15. The reagent of claim 1, wherein a molar ratio of the DPD to the inorganic chloride salt in the reagent is in a range of 1:5 to 1:40.

16. The reagent of claim 3, wherein a molar ratio of the DPD to the one or more strong acids in the reagent is in a range of 2:1 to 1:5.

* * * * *